US006184246B1

(12) United States Patent
Manthey et al.

(10) Patent No.: US 6,184,246 B1
(45) Date of Patent: Feb. 6, 2001

(54) INHIBITION OF CYTOKINE PRODUCTION BY POLYMETHOXYLATED FLAVONES

(75) Inventors: John A. Manthey, Auburndale, FL (US); Carl L. Manthey, Exton, PA (US); Antonio Montanari, Charlotte, NC (US)

(73) Assignees: The United States of America as represented by the Secretary of Agriculture, Washington, DC (US); Amgen, Inc., Thousand Oaks, CA (US)

( * ) Notice: Under 35 U.S.C. 154(b), the term of this patent shall be extended for 0 days.

(21) Appl. No.: 09/364,094

(22) Filed: Jul. 30, 1999

(51) Int. Cl.[7] .................................................. A61K 31/38
(52) U.S. Cl. ........................................ 514/456; 514/457
(58) Field of Search .................................. 514/456, 449, 514/457

(56) References Cited

U.S. PATENT DOCUMENTS

| H1427 | 4/1995 | Briet et al. ........................... 424/85.2 |
|---|---|---|
| 3,867,541 | * 2/1975 | Robbins ................................ 514/456 |
| 3,903,266 | * 9/1975 | Robbins .................................. 514/56 |
| 4,886,806 | * 12/1989 | Walenta et al. ........................ 514/253 |
| 5,013,852 | * 5/1991 | Walenta et al. ........................ 549/362 |
| 5,096,906 | 3/1992 | Mandell et al. ....................... 514/263 |
| 5,336,685 | 8/1994 | Prochaska et al. .................... 514/455 |
| 5,399,584 | * 3/1995 | Ares et al. ............................. 514/432 |
| 5,443,839 | * 8/1995 | Meybeck ............................... 424/450 |
| 5,547,970 | 8/1996 | Weithmann et al. ................... 514/378 |
| 5,646,154 | 7/1997 | Irie et al. ............................... 514/260 |
| 5,658,949 | 8/1997 | Aggarwal .............................. 514/557 |
| 5,792,448 | * 8/1998 | Dubief et al. ......................... 424/701 |
| 5,847,123 | 12/1998 | Yokoyama et al. ................... 540/529 |
| 5,877,151 | 3/1999 | Pereira .................................... 514/12 |
| 5,900,430 | 5/1999 | Badger et al. ......................... 514/409 |
| 5,900,434 | 5/1999 | Pyun et al. ............................ 514/557 |

OTHER PUBLICATIONS

Tatum, J.H., et al., "Six New Flavonoids From Citrus", *Phytochemistry,* vol. 11, pp. 2283–2288, 1972.
Chen, J., et al., "Two New Polymethoxylated Flavones, a Class of Compounds with Potential Anticancer Activity, Isolated from Cold Pressed Dancy Tangerine Peel Oil Solids", *J. Agric. Food Chem.,* vol. 45(2), pp. 364–368, 1997.
Middleton, E., et al., "Tumor promoter–induced basophil histamine release: effect of selected flavonids", *Biochemical Pharmacology,* vol. 36(12), pp. 2048–2052, 1987.
Ballesteros, J.F., et al., "Synthesis and Pharmacological Evaluation of 2'–Hydroxychalcones and Flavones as Inhibitors of Inflammatory Mediators Generation", *J. Med. Chem.,* vol. 38(14), pp. 2794–2797, 1995.
Gerritsen, M.E., et al., "Flavonoids Inhibit Cytokine–Induced Enodtheial Cell Adhesion Protein Gene Expression", *American Journal of Pathology,* vol. 147(2), pp. 278–292, 1995.

Montanari, A., et al., Citrus Flavonoids: A Review of Past Biological Activity Against Disease, in: Flavonoids in the Living System, Manthey and Buslig (eds.), Plenum Press, New York, pp. 103–116, 1998.
Internet Reference, *Doctor's Guide to Medical & Other News,* "TNF Shown to Be a Principal Trigger of Allergic Asthma in Animal Models", 1996.
Horowitz, R.M., et al., "Flavonoid Constituents of Citrus", in: Citrus Science and Technology, S. Nagy, P.E. Shaw, and M.K. Veldhuis (eds.), Avi Publishing Co., Inc., Westport, Conn., vol. 1, pp. 397–426, 1977.
Nikaido, T., et al., "Inhibition of Cyclic AMP Phosphodiesterase by Flavonoids", *Medicinal Plant Research,* vol. 46, pp. 162–166, 1982.
Manthey, J.A., et al., Abstract 050, "Methoxylated Citrus Flavones Suppress Cytokine Expression By Monocytes", Abstracts of Papers—Part 2, American Chemical Society, 216th ACS National Meeting 0–8412–3627–5, Boston, MA, Aug. 23–27, 1998.
Freedman, L., et al., "Citrus Flavonoid Complex: Chemical Fractionation and Biological Activity", *Science,* pp. 344–345, 1963.
Kawaguchi, K., et al., "Suppression of lipopolysaccharide–induced tumor necrosis factor–release and liver injury in mice by naringin", *European Journal of Pharmacology,* vol. 368, pp. 245–250, 1999.
Manthey, J.A., et al., "Polymethoxylated Flavones Derived from Citrus Suppress Tumor Necrosis Factor–alpha Expression by Human Monocytes", *Journal of Natural Products,* vol. 62(3), pp. 441–444, 1999.
Lale et al., Ability of Different Flavonoids to inhibit . . . , J. Nat. Prod., vol. 59/3, pp. 273–6, (1996).*
Louis et al., Interleukin –10 controls neutrophilic . . . , Hepatology, vol. 28/6, pp. 1607–1615 (1998).*
Hurme et al., Gene polymorphisms of interleukins 1 and 10 . . . , Ann. Med., vol. 30/5, pp. 469–473, (1998).*
Gerritsen et al., Flavonoids inhibit cytokine–induced endothelial,,,,, Am. J. Pathol., vol. 147/2, pp. 278–292, (1995).*
Panthong e tal, antiinflammatory activity of flavonoids, Phytomedicine, vol. 1/2, pp. 141–144, (1994).*
Middleton et al., The effects of citrus flavonoids on . . . , Planta med., vol. 53/4., pp. 325–328, (1987).*
Busse et al., Flavonoid modulation of human neutrophil function, J. Allergy Clin. Immunol., vol. 73/6., pp. 801–809, (1984).*

* cited by examiner

Primary Examiner—William R. A. Jarvis
Assistant Examiner—Vickie Kim
(74) *Attorney, Agent, or Firm*—M. Howard Silverstein; John D. Fado; G. Byron Stover

(57) ABSTRACT

A method of inhibiting the production of cytokines, particularly inhibiting the production of tumor necrosis factor$\alpha$, interleukin-10, and macrophage inflammatory protein-1$\alpha$ and the like, in a mammal, including a human, in need thereof which involves administering to such mammal an effective amount, preferably cytokine production inhibiting amount, of a polymethoxylated flavone.

14 Claims, 3 Drawing Sheets

INHIBITION OF CYTOKINE PRODUCTION BY POLYMETHOXYLATED FLAVONES

BACKGROUND OF THE INVENTION

This invention relates to a method of inhibiting the production of cytokines, particularly inhibiting the production of tumor necrosis factorα, interleukin-10, and macrophage inflammatory protein-1α, in a mammal, including a human, in need thereof which involves administering to such mammal an effective, cytokine production inhibiting amount of a polymethoxylated flavone.

Flavonoids are widely distributed in the plant kingdom and as many as 4000 flavonoid-related compounds have been described (Brandi, M. L., Bone Miner., 1992, (Suppl. 1), S3–14). Ingested at hundreds of mg per day in the Western diet, flavonoids appear to have several beneficial effects on human health. Of particular interest are the flavonoids derived from citrus, many of which exhibit anticancer, anticarcinogenic, antiviral, antioxidant, antithrombogenic, and antiatherogenic properties (Benavente-Garcia, O., et al., J. Agr. Food Chem., 45: 4505–4515 (1997)). Polymethoxylated flavones from citrus have been shown to reduce the invasiveness of tumors in animal models (Vermeulen, S., et al., Pathology Res. Practice, 192: 694–707 (1996)) and to induce the differentiation of myeloid leukemic cells and suppress proliferation while promoting apoptosis (Sugiyama, S., et al., Chem. Pharm. Bull., 41: 714–719 (1993); Hirano, T., et al., Brit. J. Cancer, 72: 11380–1388 (1995)). These polymethoxylated flavones have further been shown to reduce lymphocyte proliferation (Mookerjee, B. K., et al., J. Immunopharmacol., 8:371–392 (1986)), platelet aggregation (Beret, A., et al., in Plant Flavonoids in Biology and Medicine II: Biochemical, Cellular, and Medicinal Properties; Cody, V., Middleton, E. Jr., Harborne, J. B., Beretz, A., Eds.; Progress in Clinical and Biological Research 280; Alan R. Liss Inc.: New York, 1988; p 187–200), and to suppress ethanol-induced gastric hemorrhagic lesions (Takase, H., et al.,. Japan. J. Pharmacol., 66: 139–147 (1994)), while promoting chloride secretion by human colonic epithelial cells (Nguyen, T. D., et al., J. Nutrition, 123: 259–268 (1993)). The antiinflammatory properties of dietary flavonoids have also received considerable attention. Select hydroxylated flavones block adhesion molecule biosynthesis by cytokine-induced endothelial cells (Baloch, Z., et al., Cell Immunol., 160: 98–103 (1995); Gerritsen, M. E., et al., Am. J. Pathol., 147: 278–292 (1995)). In other studies, flavonoids have been shown to block activation-induced degranulation of neutrophils and mast cells (Middleton, E., Jr., et al., Biochem. Pharmacol., 43: 1167–1179 (1992)). A formulation of citrus flavonoids has been shown to block capillary leakage and leukocyte infiltration in animal models (Bouskela, E., et al., Angiology, 48: 391–399 (1997); Friesenecker, B., et al.,. Int. J. Microcirc., (suppl. 1), 17–21 (1995).

Central to many aspects of inflammation are the cytokines which behave as autocrine or paracrine protein factors. In particular, the cytokine, tumor necrosis factor-α (TNFα), drives many critical components of inflammatory processes (Feldmann, M., et al., Annu. Rev. Immunol., 14: 397–440 (1996); Moreland, L. W., N. Engl. J. Med., 337:141–147 (1997)). Monocytes are a major cellular source of TNFα and other cytokines. Recently the main flavanone glycoside in grapefruit, naringin, has been reported to suppress lipopolysaccharide-induced TNFα release and liver injury in mice (Kawaguchi, K., et al., Eur. J. Pharmacol., 368: 245–250 (1999)). However, apparently there have been no reports of polymethoxylated flavonoids inhibiting the production of cytokines (e.g., tumor necrosis factorα, interleukin-10, macrophage inflammatory protein-1α).

SUMMARY OF THE INVENTION

This invention provides a method of inhibiting the production of cytokines, particularly inhibiting the production of tumor necrosis factorα, interleukin-10, and macrophage inflammatory protein-1α, in a mammal, including a human, in need thereof which involves administering to such mammal an effective amount, preferably cytokine production inhibiting amount, of a polymethoxylated flavone.

DETAILED DESCRIPTION OF THE INVENTION

Figure 1:
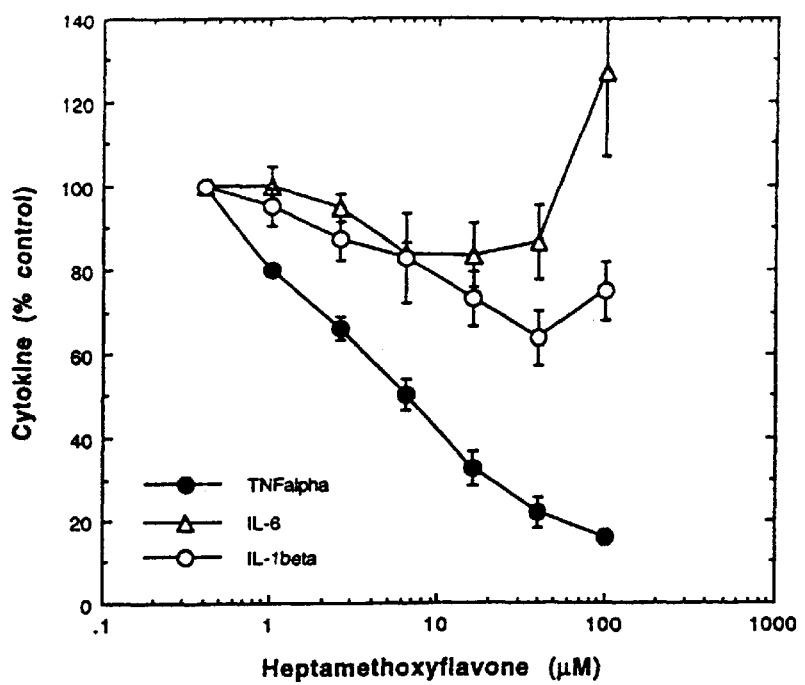
FIG. 1 shows the effect of HMF (3,5,6,7,8,3',4'-heptamethoxyflavone) on cytokine expression by LPS-stimulated monocytes. Adherent purified human monocytes were cultured in the presence of graded concentrations of heptamethoxyflavone for 30 min. The monocyte cultures were then adjusted to contain 20 ng/mL LPS. After 14 h of culture, the cytokines TNFα, IL-6, IL-8, MIP-1α, and IL-10 were assayed in the culture supernatants and IL-1β was assayed in the cell lysates using specific ELISA assays as described below. Values expressed as the percent of cytokine produced in flavone-free cultures are the means and standard errors determined using monocytes isolated from three independent donors.
Figure 1:
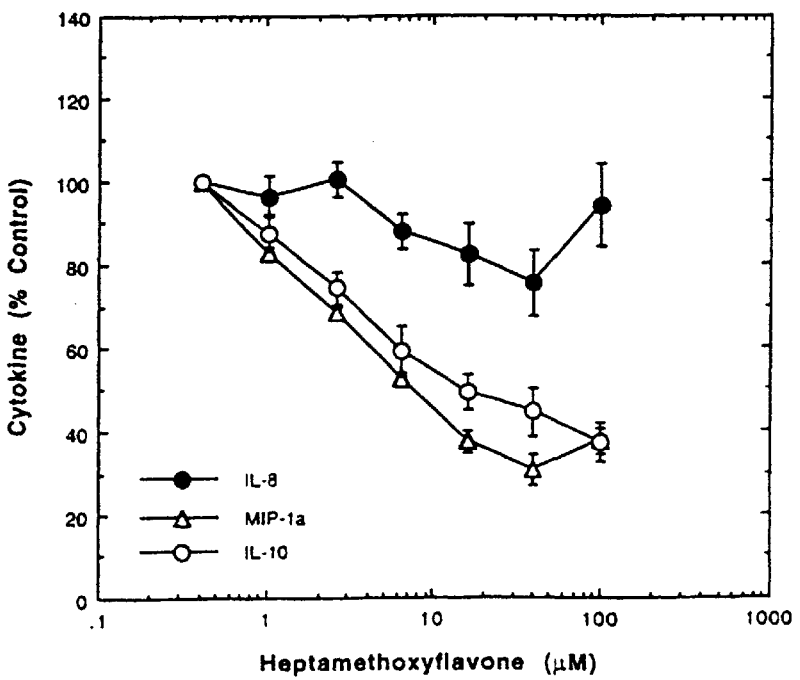

The present invention relates to the treatment of any disease or disorder mediated by cytokines (e.g., tumor necrosis factorα, interleukin-10, macrophage inflammatory protein-1α and the like; especially tumor necrosis factorα), such as diseases or disorders caused or characterized by excessive or undesirable production of cytokines (e.g., tumor necrosis factorα, interleukin-10, macrophage inflammatory protein-1α and the like; especially tumor necrosis factorα). Examples of such diseases include but are not limited to septic shock, cancer, cachexia, chronic rheumatism, ulcerative colitis, Crohn's disease, and many other diseases and disorders mediated by cytokines (e.g., tumor necrosis factorα, interleukin-10, macrophage inflammatory protein-1α and the like). The present invention also relates to a method of inhibiting the production of cytokines (e.g., tumor necrosis factorα, interleukin-10, macrophage inflammatory protein-1α and the like; especially tumor necrosis factorα) by administering to a mammal (such as mouse, rat, sheep, goat, human, pig, horse, and the like, preferably human) in need of such treatment an effective amount, preferably cytokine production inhibiting amount, of a polymethoxylated flavone. The present invention also relates to a method of inhibiting the production of cytokines (e.g., tumor necrosis factorα, interleukin-10, macrophage inflammatory protein-1α and the like; especially tumor necrosis factorα) by administering to a mammal in need of such treatment a therapeutically effective amount of a polymethoxylated flavone.

Several hydroxylated flavones were tested and found to be active as TNFα inhibitors. However, the hydroxylated flavones were also found to be cytotoxic to human monocytes. Surprisingly, when several polymethoxylated flavones of the invention were tested, they were found to be highly active TNFα inhibitors and had negligible cytotoxicity in human monocytes.

Administering polymethoxylated flavones of the invention to a mammal results in a reduction in the amount of cytokines (e.g., tumor necrosis factorα, interleukin-10, macrophage inflammatory protein-1α and the like; especially tumor necrosis factorα) present in the mammal, preferably a reduction of the serum, plasma or whole blood concentration or in vivo amount of cytokines. Preferably the concentration or in vivo amount of cytokines is reduced to normal levels typically found in such a mammal. Without being bound by any particular mechanism, the polymethoxylated flavones of the invention appear to reduce the concentration or in vivo amount of cytokines present in the treated mammal by inhibiting the production of the cytokines or reducing the amount produced or the rate of production of the cytokines. Also, preferably, the polymethoxylated flavones of the invention are administered in amounts in which little or no cytotoxicity (e.g, as determined in vitro by measuring lactate dehydrogenase (LDH) content of cell lysates as described below), more preferably no cytotoxicity, is detected. A "polymethoxylated flavone" is a flavone substituted by methoxy groups, preferably at least 2, more preferably at least 3, more preferably at least four, more preferably 4–8, and most preferably 4–7 methoxy groups and optionally substituted by one or more hydroxy groups, preferably 1–3, and more preferably 1–2 hydroxy groups.

Preferably the polymethoxylated flavone is derived from citrus. More preferably, the polymethoxylated flavone is selected from the group consisting of 5,6,7,8,4'-pentamethoxyflavone (tangeretin), 3,5,6,7,8,3',4'-heptamethoxyflavone, 5,6,7,8,3',4'-hexamethoxyflavone (nobiletin), 5,6,7,3',4'-pentamethoxyflavone (sinensetin), 5-hydroxy -6,7,8,3',4'-pentamethoxyflavone, 5,7,8,3',4'-pentamethoxyflavone, 7-hydroxy-3,5,6,7,3',4'-hexamethoxyflavone, 5-hydroxy-3,6,7,8,3',4'-hexamethoxyflavone, 5,6,7,3',4',5'-hexamethoxyflavone, 5,7,3',4'-tetramethoxyflavone, and mixtures thereof. Most preferably the polymethoxylated flavone is 3,5,6,7,8,3',4'-heptamethoxyflavone.

The isolation and syntheses of the flavonoids 5,6,7,8,4'-pentamethoxyflavone (tangeretin), 3,5,6,7,8,3',4'-heptamethoxyflavone, 5,6,7,8,3',4'-hexamethoxyflavone (nobiletin), 5,6,7,3',4'-pentamethoxyflavone (sinensetin), 5-hydroxy-6,7,8,3',4'-pentamethoxyflavone, 5,7,8,3',4'-pentamethoxyflavone, 7-hydroxy-3,5,6,7,3',4'-hexamethoxyflavone, and 5-hydroxy -3,6,7,8,3',4'-hexamethoxyflavone were previously reported in the following references (all of which are incorporated herein by reference in their entirety): Chen, J., et al., J. Agric. Food Chem., 45: 364–368 (1997); Tatum, J. H., et al., Phytochem., 11: 2283–2288 (1972); Swift, L. J., J. Agric. Food Chem., 13: 431–433 (1965a); Swift, L. J., J. Org. Chem., 30, 2079 (1965b); R. M. Horowitz and B. Gentili, (1977), Flavonoid Constituents in Citrus, in: Citrus Science and Technology, S. Nagy, P. E. Shaw, and M. K. Veldhuis (Eds.), Avi Publishing Company, Inc., Westport, Conn. 5,6,7,3',4',5'-hexamethoxyflavone and 5,7,3',4'-tetramethoxyflavone can be produced by methods described by H. Wagner L. and Farkas, "Synthesis of Flavonoids" in: The Flavonoids, J. B. Harbome, T. J. Mabry, H. Mabry (Eds.), Academic Press, NY, pp127–213 (which is incorporated herein by reference in its entirety).

The methods of the present invention may be administered to any mammal. Most preferably, the polymethoxylated flavones useful in the methods of the present invention are administered to a human.

In another aspect of the invention, the polymethoxylated flavones may be formulated into a pharmaceutical preparation by a conventional method usually employed in the art.

Generally, the dose of the polymethoxylated flavones given in the methods of the present invention (i.e., the effective amount of a polymethoxylated flavone) is a quantity that results in a reduction in the concentration or in vivo amount of cytokines (e.g., tumor necrosis factorα, interleukin-10, macrophage inflammatory protein-1α and the like; especially tumor necrosis factorα) in the mammal. Preferably, the dose is a cytokine production inhibiting amount (e.g., a quantity of polymethoxylated flavones capable of inhibiting the production of the cytokines or reducing the amount produced or the rate of production of the cytokines). Methods of determining the effective concentrations are well known in the art. For example, a person of ordinary skill in the art can easily extrapolate the effective concentrations as determined in vitro and apply it to living mammals to determine the effective concentrations in vivo. Preferably, the dose of the polymethoxylated flavone is between 0.1–10 grams per 100 Kg body weight; most preferably between 1–10 grams per 100 Kg body weight.

By the term "cytokine production inhibiting amount" is meant an effective amount of polymethoxylated flavone which will, when given for the treatment, prophylactically or therapeutically, of any disease state which is modulated by one or more cytokines, such as diseases exacerbated or caused by excessive unregulated cytokine production, cause a decrease in the in vivo levels of the cytokine (e.g., tumor necrosis factorα, interleukin-10, macrophage inflammatory protein-1α and the like; especially tumor necrosis factorα) to normal or below normal levels.

The polymethoxylated flavone can be administered by a variety of routes, including oral, transdermal, subcutaneous, rectal, intraarticular, intravenous and intramuscular introduction. However, it should be understood that the amount of the polymethoxylated flavone actually administered ought to be determined in light of various relevant factors including the condition to be treated, the chosen route of administration, the age and weight of the individual patient, and the severity of the patient's symptom; and, therefore, the above dose should not be construed to limit the scope of the invention in any way.

The polymethoxylated flavones useful in the methods of the present invention may be administered in a pharmaceutically or physiologically acceptable carrier. The pharmaceutically or physiologicially acceptable carrier is any solvent with which the polymethoxylated flavone is compatible and which is non-toxic to the individuals treated at the amounts administered. A pharmacological dose of the polymethoxylated flavone useful in the methods of the present invention is that amount which results in a reduction in the concentration or in vivo amount of cytokines (e.g., tumor necrosis factorα, interleukin-10, macrophage inflammatory protein-1α and the like; especially tumor necrosis factorα) in the mammal. Preferably, the pharmacological dose is a cytokine production inhibiting amount of the polymethoxylated flavone.

The following examples are intended only to further illustrate the invention and are not intended to limit the scope of the invention as defined by the claims.

EXAMPLES

General Experimental Procedures: Flavonoids from citrus plant material were the authentic samples reported previously (Chen, J., et al., J. Agric. Food Chem., 45: 364–368 (1997); Tatum, J. H., et al., Phytochem., 11: 2283–2288 (1972); Swift, L. J., J. Agric. Food Chem., 13: 431–433 (1965a); Swift, L. J., J. Org. Chem., 30, 2079 (1965b); R. M. Horowitz and B. Gentili, (1977) Flavonoid Constituents in Citrus, in: Citrus Science and Technology, S. Nagy, P. E. Shaw, and M. K. Veldhuis (Eds.), Avi Publishing Company, Inc., Westport, Conn.). Purity of these citrus and the non-citrus flavonoids obtained from commercial sources were confirmed >95% by HPLC analysis at 220, 285, and 330 nm. 50 mM stocks of flavones were prepared in dimethylsulfoxide and stored at −80° C. Phenol-water extracted $E.\ coli$ K235 lipopolysaccharide was purchased from Sigma (St. Louis, Mo.).

Isolation of human peripheral blood monocytes: Peripheral blood mononuclear cells (PBMCs) were isolated from residual source leukocytes (Bonfils Blood Center, CO) by density gradient centrifugation using Ficoll-Paque Plus (Pharmacia, Sweden). Monocytes were purified further by plastic adherence (see below) or by centrifugal elutriation as described previously (Manthey, C. L., et al., J. Leuk Biol., 64: 409–416 (1998)).

Evaluation of cytokine suppressive properties of flavonoids: 30% fetal calf serum (FCS) in the culture media was optimal for flavonoid solubility and for cytokine expression by monocytes. To measure the impact of the flavones on cytokine production, PBMCs were resuspended to $4\times10^6$/mL in complete medium, i.e., Dulbecco's Modified Eagle Medium containing 30% FCS, 2 mM glutamine, 100 U/mL Penicillin-G, and 100 μg/mL streptomycin. 100 μL of cell suspension was dispensed into each well of FALCON 96-well Microtest Tissue Culture Plates (Becton Dickinson, Franklin Lakes, N.J.) and cultured 2 h at 3720 C. and 5% $CO_2$. Nonadherent cells (lymphocytes) were separated from the plastic adherent cells (monocytes) by washing the wells twice with 200 μL of medium. The monocytes were cultured an additional 30 min in 100 μL of complete medium containing graded concentrations of the compound of interest and the cultures were then adjusted to contain 10 ng/mL LPS to stimulate cytokine production. Culture supernatants were harvested 14 h later, and cells were lysed by addition of 50 μL of Dulbecco's phosphate buffered saline containing 1% NP40. Culture supernatants were evaluated for TNFα, IL-1β, IL-6, IL-8, IL-10, and MIP-1α content using specific enzyme-linked immunosorbent assays (ELISA) purchased from R&D Systems. IL-1β was measured in cell lysates by ELISA. Lactate dehydrogenase (LDH) content of cell lysates was measured to determine compound effects on cell viability: To 50 μL of lysate were added 200 μL of 50 mM sodium pyrophosphate buffer (pH 8.9) containing 50 mM lactic acid and 4 mg/mL β-nicotinamide adenine dinucleotide (Sigma); rates of reduction of nicotinamide adenine dinucleotide were measured at room temperature at 340 nm.

Testing flavones as phosphodiesterase inhibitors and inducers of cellular cyclic adenosine monophosphate (cAMP): The Phosphodiesterase cAMP SPA Enzyme Assay (Amersham, Arlington Heights, Ill.) was used to test the ability of flavones to inhibit cAMP hydrolysis catalyzed by phosphodiesterase. The phosphodiesterase used in this study was semi-purified from U937 cells, and was determined to be mostly the type-IV isoform based on sensitivity to selected isoform inhibitors (Trophy, T. J., J. Pharmacol. Experimental Therapeutics, 1195–1205 (1992)).

To test flavones for the ability to cause an increase in cellular cAMP, monocytes were purified from PBMC by centrifugal elutriation. Monocytes were resuspended to $5\times10^6$/mL in complete medium and 2 mL cell suspension were dispensed into FALCON 17×100 mm polypropylene culture tubes (Becton Dickinson). The cells were precultured 2 h at 37° C. and 5% $CO_2$, and then cultured an additional 30 min following adjusting culture media to contain 100 μM of the flavone of interest or 200 μM IBMX (3-isobutyl-1-methylxanthine). Cells were then collected by centrifugation, lysed in 300 μL of ice cold aqueous solution containing 10 mM HEPES (pH 7.6) and 1% NP40. The lysates were applied to 100 mg columns of Amprep SAX resin (Amersham). The columns were then rinsed with 1 mL of methanol and the cAMP was eluted in 600 μL of methanol containing 0.01 M HCl. The eluates were chilled on dry ice and dried under vacuum. The Amersham Biotrak cAMP EIA assay was used to measure cAMP content of residues resuspended in 400 μL of assay buffer.

Analysis of specific mRNA levels by reverse transcriptase-polymerase chain reaction (RT-PCR): Monocytes were purified from PBMC by centrifugal elutriation. Monocytes were resuspended to $5\times10^6$/mL in complete medium and 2 mL of cell suspension were dispensed into FALCON 17×100 mm polypropylene culture tubes (Becton Dickinson). Cultures were adjusted to contain graded concentrations of HMF and cultured 30 min at 37° C. and 5% $CO_2$. Cultures were then adjusted to contain 20 ng/mL LPS for an additional 90 min. Culture media was then removed and monocytes were lysed in RNAzol (Teltext Inc., Friendswood, Tex.) and total RNA was isolated according to the manufacturer's instructions. Relative levels of TNFα and IL-1β mRNA were then measured by RT-PCR as previously described (Manthey, C. L., J. Leuk Biol. 1998, 64: 409–416). PCR was carried out in the presence of [α-$^{32}$P]dCTP. Radiolabeled products were resolved by agarose gel electrophoresis and quantified using a PhosphorImager (Molecular Dynamics, Sunnyvale, Calif.). For these reactions, the following primer sets were used:

GAPDH, (5'): TGA AGG TCG GAG TCA ACG GAT TTG GT, (3'): CAT GTG GGC CAT GAG GTC CAC CAC;
TNFα, (5'): ATG AGC ACT GAA AGC ATG ATC; (3'): TCA CAG GGC AAT GAT CCC AAA GTA GAC CTG CCC;
IL-1β, (5'): GAC ACA TGG GAT AAC GAG GCT, (3'): ACG CAG GAC AGG TAC AGA TTC.

An extensive collection of flavonoids from citrus was evaluated for the suppression of TNFα production in cultures of human monocytes. Of these compounds, the polymethoxylated flavones consistently showed the highest inhibition of TNFα production (Table 1). The $IC_{50}$ values for these compounds occurred in a narrow range of 5 to 30 μM. With the exception of tetra-O-methylscutellarein, surprisingly there was negligible cytotoxicity detected with these compounds. The citrus flavanone- and flavone-O- and C-glycosides, naringin, hesperidin, diosmin, isosakuranetin rutinoside, narirutin, margaretin, isomargaretin, and isovitexin were inactive as inhibitors ($IC_{50}$>200 μM), and showed no cytotoxicity (data not shown). A number of polyhydroxylated flavone aglycones were inhibitory towards TNFα production but were also significantly cytotoxic towards cultured human monocytes as measured by depletion of cellular LDH activity (Table 1). Significantly, other polyhydroxylated flavonoid aglycones, including myricetin, hesperetin, fisetin, chrysin, epicatechin, baicalein, galagin, 7-hydroxyflavone, 3-hydroxyflavone, catechin, flavanone, 4,5,6-trihydroxyflavone, 3,4,7-trihydroxyflavone, eriodictyol, gossypetin, and robinin, lacked activity and any associated cytotoxicity (data not shown).

The inhibition of cytokine production by the polymethoxylated flavones was further characterized by determining the ability of 3,5,6,7,8,3',4'-heptamethoxyflavone (HMF) to inhibit the production of the other main monocyte-derived cytokines, including IL1β, IL-6, IL-8, IL-10, and MIP-1α. The ability of HMF ($IC_{50,TNF\alpha}$=5 μM) to modulate the production of these other cytokines was evaluated in monocytes from three independent human donors. These studies showed that HMF was a potent inhibitor of the induced expression of not only TNFα, but also of IL-10, and MIP-1α (FIG. 1). $IC_{50}$ values for HMF inhibition of IL-10 and MIP-1α were 12.3±3.5 and 7.3±0.7 μM, respectively. In contrast, there was no inhibition at 100 μM HMF of the lipopolysaccharide-induced expression of IL-1β, IL-6, or IL-8. In fact, the expression of IL-6 was increased 30% in the presence of 100 μM HMF.

Figure 2:
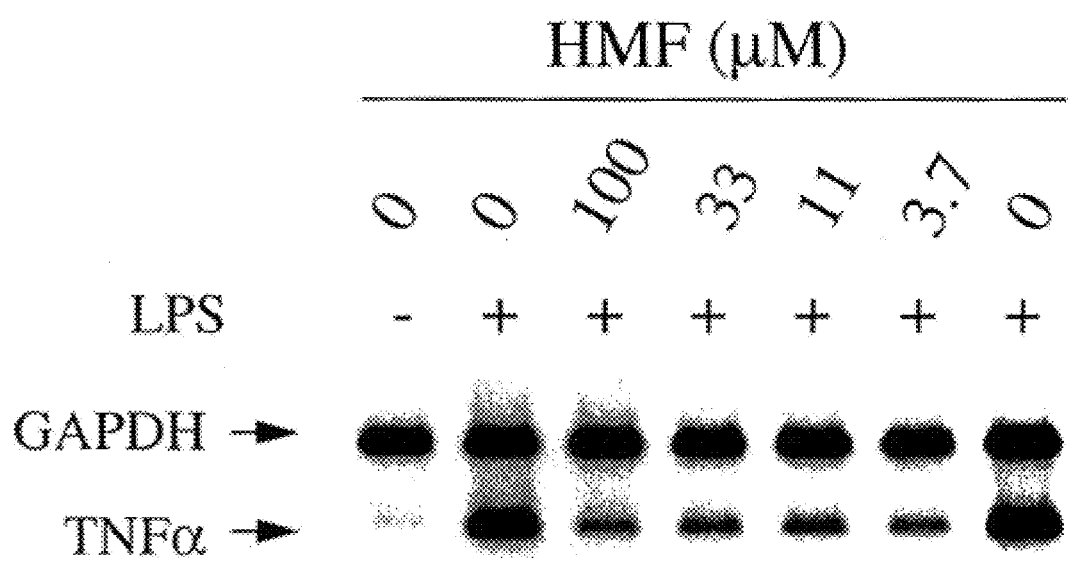
FIG. 2 shows that HMF selectively blocks expression of TNF mRNA. Primary elutriated human monocytes were cultured in the presence of graded concentrations of HMF for 30 min. The monocyte cultures were then adjusted to contain 20 ng/mL LPS. At 90 min of culture, monocytes were harvested by centrifugation, and RNA was isolated from the cell pellet. Relative levels of TNFα and the constitutively expressed glyceraldehyde 3-phosphate dehydrogenase (GAPDH) mRNA were determined by RT-PCR as described below.

To provide insight into how HMF blocks TNFα production, monocytes were activated with bacterial lipopolysaccharides in the presence or absence of HMF, and TNFα mRNA was quantified by RT-PCR. In these experiments, mRNA encoding the constitutively-expressed gene, glyceraldehyde 3-phosphate dehydrogenase (GAPDH), was also measured to serve as an internal standard. The ability of HMF to suppress TNF protein production correlated with the ability of HMF to suppress lipopolysaccharide-induced TNFα mRNA expression (FIG. 2). Significantly, the induction of IL-1β mRNA was not effected (data not shown), consistent with the lack of effect of this compound on the production of IL-1β protein.

Figure 3:
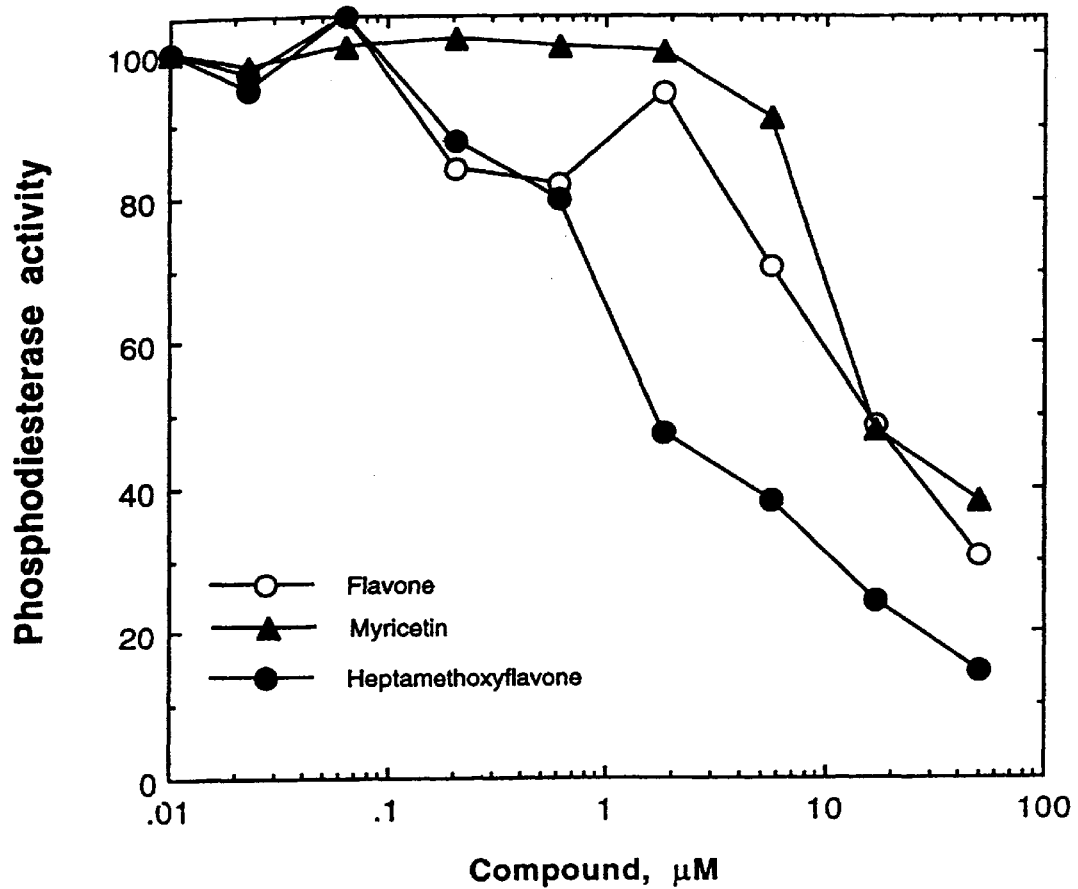
FIG. 3 shows the inhibition of PDE (phosphodiesterase) activity by HMF. PDE semipurified from U937 monocytic cells was evaluated for the ability to catalyze the hydrolysis of cAMP in the presence of graded concentrations of flavone, myricetin, and HMF as described below. The rates are plotted as percent of control-reactions, where no flavonoids were present.

Flavones have been previously shown to inhibit phosphodiesterase, the enzyme that catalyzes the hydrolysis of cyclic adenosine monophosphate (cAMP)(Nikaido, T., et al., J. Med. Plant Res., 46: 162–166 (1982); Beret, A., et al., in Plant Flavonoids in Biology and Medicine II: Biochemical, Cellular, and Medicinal Properties; Cody, V., Middleton, E., Jr. Harborne, J. B., Beretz, A., Eds.; Progress in Clinical and Biological Research 280; Alan R. Liss Inc.: New York, 1988, p 281–296; Petkov, E., et al., Planta Medica, 43: 183–186 (1981); Nikaido, T., et al., Chem. Pharm. Bull., 36: 654–661 (1988)). Some phosphodiesterase inhibitors are also known to suppress TNFα production (Semmler, J., et al., Int. J. Immunopharmacol., 15: 409–413 (1993)). We sought to determine if the ability of HMF to suppress TNFα production correlated with an ability to inhibit phosphodiesterase since it was unknown whether the ability of PMFs to suppress TNFα production also correlated with the ability to inhibit phosphodiesterase. HMF was compared with flavone and myricetin which are much less active at inhibiting TNFα production. Graded concentrations of HMF, flavone, or myricetin were added to enzyme reaction mixtures containing cAMP and type-IV phosphodiesterase semi-purified from a monocyte cell line. Hydrolysis of cAMP was used to measure phosphodiesterase activity (FIG. 3). Phosphodiesterase activity was inhibited 50% by 2, 11, and 16 μM with HMF, flavone, and myricetin respectively. The order of potency was consistent with the superior ability of HMF to inhibit TNFα production. The HMF inhibition of monocyte phosphodiesterase was further demonstrated by the elevated cytosolic cAMP that occurred after treating the activated human monocytes for 30 minutes in the presence of 100 μM HMF, flavone, or myricetin. The cAMP was subsequently quantitated in cell extracts using a specific ELISA. Other cells were treated with 200 μM of 3-isobutyl-1-methylxanthine (IBMX), a known potent inhibitor of phosphodiesterase that served as a positive control. In cells cultured in media alone the levels of intracellular cAMP were 2.7±0.9 pmol/$10^7$ cells whereas in cells cultured in the presence of 100 μM myrecitin, flavone, HMF, or 200 μM IBMX, the levels were 3.7±1.0, 3.6±1.1, 5.7±1.8, and 8.3±1.9 pmol/$10^7$ cells, respectively. Hence, both HMF and IBMX caused at least a doubling of the monocyte cAMP levels, whereas the increases resulting from the presence of flavone and myricetin were much less.

To further evaluate if phosphodiesterase inhibition represents an important mechanism of action for HMF, the cytokine suppression profile of HMF was compared against the suppression profile of IBMX (Table 2). Both compounds produced a similar reduction in TNFα and MIP-1α, and neither suppressed the production of IL-1β, IL-6 and IL-8. Based on these similarities, we conclude that the mode of action of HMF may be similar to that of IBMX. However, distinct from HMF, IBMX did not inhibit IL-10 production. This inhibition of IL-10 production by HMF suggests that there are other yet uncharacterized aspects of the inhibitory properties of HMF towards activated human monocytes. Finally, it is of interest that polymethoxylated flavones have been shown to not inhibit protein kinase C, and they exhibit minimal antioxidant activity (Ferriola, P. C., et al., Biochem. Pharmacol., 38: 1617–1624 (1989); Kandaswami, C., et al., in Free Radicals in Diagnostic Medicine, D. Armstrong Ed.; Plenum Press: New York, 1994, p 351–376). Thus, these mechanisms, widely applicable to other flavonoids (Middleton, E., Jr., in Flavonoids in the Living System, Manthey, J. A., Buslig, B. S., Eds.; Plenum Press: New York, 1998, p 175–182), are not involved in our studies.

The ability of polymethoxylated flavones to treat or prevent septic shock (caused by endotoxins which lead to the excessive production of cytokines such as tumor necrosis factorα) can be determined by the hyperdynamic model described in U.S. Pat. No. 5,877,151. Furthermore, the ability of polymethoxylated flavones to inhibit the production of cytokines in vivo can be determined by the models described in U.S. Pat. Nos. 5,900,434, 5,847,123 and 5,646, 154, and in the journal article by Badger, A. M., et al., J. Pharmacol. Exp. Ther., 279:1453–61(1996).

All of the above cited references are incorporated herein by reference in their entirety. The following U.S. Patents are incorporated herein by reference in their entirety: U.S. Pat. Nos. 5,096,906; 5,336,685; 5,547,970; 5,646,154; 5,658, 949; 5,847,123; 5,877,151; 5,900,430; 5,900,434. Statutory Invention Registration H1427 is incorporated herein by reference in its entirety. J. Nat. Prod. 1999, 62: 441–444 is incorporated herein by reference in its entirety.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method of inhibiting the production of cytokines, comprising administering to a mammal in need of such treatment an effective, cytokine production inhibiting amount of a polymethoxylated flavone.

2. The method according to claim 1, wherein said cytokines are selected from the group consisting of tumor necrosis factorα, interleukin-10, macrophage inflammatory protein-1α, and mixtures thereof.

3. The method according to claim 2, wherein said cytokine is tumor necrosis factorα.

4. The method according to claim 1, wherein said polymethoxylated flavone is selected from the group consisting of 5,6,7,8,4'-pentamethoxyflavone, 3,5,6,7,8,3',4'-heptamethoxyflavone, 5,6,7,8,3',4'-hexamethoxyflavone, 5,6,7,3',4'-pentamethoxyflavone, 5-hydroxy-6,7,8,3',4'-pentamethoxyflavone, 5,7,8,3',4'-pentamethoxyflavone, 7-hydroxy-3,5,6,7,3',4'-hexamethoxyflavone, 5-hydroxy-3,6,7,8,3',4'-hexamethoxyflavone, 5,6,7,3',4',5'-hexamethoxyflavone, 5,7,3',4'-tetramethoxyflavone, and mixtures thereof.

5. The method according to claim 4, wherein said polymethoxylated flavone is 5,6,7,8,3',4'-hexamethoxyflavone.

6. The method according to claim 1, wherein said mammal is a human.

7. The method according to claim 1, wherein said effective, cytokine production inhibiting amount is 0.1–10 grams per 100 Kg body weight.

8. The method according to claim 7, wherein said effective, cytokine production inhibiting amount is 1–10 grams per 100 Kg body weight.

9. A method of reducing the in vivo amount of cytokines in a mammal, comprising administering to said mammal an effective amount of a polymethoxylated flavone.

10. The method according to claim 9, wherein said cytokines are selected from the group consisting of tumor necrosis factorα, interleukin-10, macrophage inflammatory protein-1α, and mixtures thereof.

11. The method according to claim 10, wherein said cytokine is tumor necrosis factorα.

12. The method according to claim 9, wherein said polymethoxylated flavone is selected from the group consisting of 5,6,7,8,4'-pentamethoxyflavone, 3,5,6,7,8,3',4'-heptamethoxyflavone, 5,6,7,8,3',4'-hexamethoxyflavone, 5,6,7,3',4'-pentamethoxyflavone, 5-hydroxy-6,7,8,3',4'-pentamethoxyflavone, 5,7,8,3',4'-pentamethoxyflavone, 7-hydroxy-3,5,6,7,3',4'-hexamethoxyflavone, 5-hydroxy-3,6,7,8,3',4'-hexamethoxyflavone, 5,6,7,3',4',5'-hexamethoxyflavone, 5,7,3',4'-tetramethoxyflavone, and mixtures thereof.

13. The method according to claim 12, wherein said polymethoxylated flavone is 5,6,7,8,3',4'-hexamethoxyflavone.

14. The method according to claim 9, wherein said mammal is a human.

* * * * *